United States Patent
Chiou et al.

(10) Patent No.: US 11,679,067 B2
(45) Date of Patent: Jun. 20, 2023

(54) COSMETIC COMPOSITIONS

(71) Applicant: L'Oreal, Paris (FR)

(72) Inventors: Catherine Chiou, Saddle Brook, NJ (US); Angelike Galdi, Westfield, NJ (US); Kun Qian, Millburn, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 17/362,002

(22) Filed: Jun. 29, 2021

(65) Prior Publication Data

US 2021/0401684 A1 Dec. 30, 2021

Related U.S. Application Data

(60) Provisional application No. 63/046,574, filed on Jun. 30, 2020.

(30) Foreign Application Priority Data

Oct. 16, 2020 (FR) ...................... 2010660

(51) Int. Cl.
*A61K 8/02* (2006.01)
*A61K 8/06* (2006.01)
*A61K 8/34* (2006.01)
*A61K 8/44* (2006.01)
*A61Q 19/08* (2006.01)
*A61K 8/20* (2006.01)
*A61K 8/25* (2006.01)
*A61K 8/29* (2006.01)
*A61K 8/81* (2006.01)
*A61K 8/89* (2006.01)

(52) U.S. Cl.
CPC ............... *A61K 8/064* (2013.01); *A61K 8/20* (2013.01); *A61K 8/25* (2013.01); *A61K 8/29* (2013.01); *A61K 8/8152* (2013.01); *A61K 8/89* (2013.01); *A61Q 19/08* (2013.01); *A61K 2800/43* (2013.01); *A61K 2800/524* (2013.01); *A61K 2800/621* (2013.01)

(58) Field of Classification Search
None
See application file for complete search history.

(56) References Cited

U.S. PATENT DOCUMENTS

| | | | |
|---|---|---|---|
| 6,258,345 B1 | 7/2001 | Rouquet et al. | |
| 10,758,476 B1 | 9/2020 | Moss et al. | |
| 2002/0037261 A1 | 3/2002 | Lapidot et al. | |
| 2004/0009131 A1* | 1/2004 | Simonnet | A61K 8/064 424/63 |
| 2012/0134939 A1 | 5/2012 | Ueda et al. | |
| 2016/0089312 A1* | 3/2016 | Dique-Mouton | A61K 8/064 424/63 |
| 2019/0201304 A1 | 7/2019 | Sverdlove et al. | |
| 2020/0352844 A1 | 11/2020 | Thevenet et al. | |

FOREIGN PATENT DOCUMENTS

| | | |
|---|---|---|
| FR | 2768926 A1 | 4/1999 |
| FR | 3004644 A1 | 10/2014 |
| FR | 3042409 A1 | 4/2017 |
| FR | 3073146 A1 | 5/2019 |
| JP | 2001335434 A | 12/2001 |
| JP | 2009235046 A | 10/2009 |

OTHER PUBLICATIONS

Anonymous, https://www.ulprospector.com/en/eu/PersonalCarelDetaiV109955/1563349/NXT-SOLV-300, downloaded from the internet Jun. 30, 2021, 2 pages.
Anonymous, https://www.ulprospector.com/en/eu/PersonalCare/Detail/109955/1563350/NXT-SOLV-400?, downloaded from the internet Jun. 30, 2021, 2 pages.
French Search Report for French Application No. 2010660, dated Jul. 8, 2021, 14 pages.
International Search Report and Written Opinion for International Application No. PCT/US2021/039099, dated Sep. 13, 2021, 20 pages.

* cited by examiner

*Primary Examiner* — Brian Gulledge
(74) *Attorney, Agent, or Firm* — RatnerPrestia

(57) ABSTRACT

A composition is provided. The composition is a water-in-oil emulsion comprising an aqueous phase and an oil phase. The aqueous phase comprises water, one or more humectants, one or more preservatives, one or more preservative boosters, one or more stabilizers and/or one or more pH adjusters. The oil phase comprises one or more solvents, one or more emulsifiers, one or more emollients and/or one or more aesthetic modifiers. Methods of preparing the composition and methods of improving the appearance of skin are also provided.

9 Claims, 2 Drawing Sheets

COSMETIC COMPOSITIONS

CROSS-REFERENCE TO RELATED APPLICATIONS

This application claims the benefit of U.S. Provisional Application No. 63/046,574, filed Jun. 30, 2020, and French Patent Application No. 2010660, filed on Oct. 16, 2020, the contents of each of which are incorporated herein by reference in their entireties for all purposes.

FIELD OF THE INVENTION

The invention relates to new cosmetic composition for improving the appearance of skin by reducing the appearance of fine lines, wrinkles, and imperfection of skin appearance and texture in a consumer-pleasing texture and for boosting healthy skin glow upon application.

BACKGROUND OF THE INVENTION

Glycerin has been shown to have anti-aging benefits based on previous clinical studies.

Retinol has also been well studied for its anti-aging benefit, and is often served as a benchmark for anti-aging. Particularly, stabilized retinol at 0.15% is often considered as a top performer for anti-aging benefits, but incidences of skin irritation were often noted.

On the other hand, makeup products containing aesthetic modifiers often provide consumers with pleasing texture and for boosting healthy skin glow upon application.

SUMMARY OF THE INVENTION

The present invention relates to a stable and efficacious water-in-oil emulsion system with 10% glycerin, polyacid esters and/or ethyl acetal levulinate derivatives, and aesthetic modifiers, including functional fillers and effect pigments for improving the appearance of skin by reducing the appearance of fine lines, wrinkles, and imperfection of skin appearance and texture in a consumer-pleasing texture and for boosting healthy skin glow upon application.

The inventors have unexpectedly discovered that the combination of polyacid esters and/or ethyl acetal levulinate derivatives with glycerin and aesthetic modifiers provided surprisingly effective anti-aging benefits, and an instant optical effect for reducing the appearance of fine lines and wrinkle and imperfections on skin.

A composition is provided. The composition comprises an aqueous phase and an oil phase. The aqueous phase comprises water, one or more humectants, and one or more preservatives, preservative boosters and/or stabilizers. The oil phase comprises one or more solvents, one or more emulsifiers, one or more emollients and/or one or more aesthetic modifiers. The one or more solvents are selected from the group consisting of diisopropyl adipate, diisopropyl sebacate, ethyl PG-acetal levulinate, ethyl glycerin acetal levulinate, triethyl citrate and a combination thereof. The composition is a water-in-oil emulsion.

The one or more solvents may be selected from the group consisting of diisopropyl adipate, diisopropyl sebacate, ethyl PG-acetal levulinate, ethyl glycerin acetal levulinate, triethyl citrate and a combination thereof. The one or more solvents may be diisopropyl adipate and diisopropyl sebacate. The one or more solvents may be diisopropyl adipate and ethyl PG-acetal levulinate. The one or more solvents may be diisopropyl adipate and ethyl glycerin acetal levulinate. The one or more solvents may be diisopropyl adipate and triethyl citrate.

The oil-phase further comprises one or more aesthetic modifiers, which include both at least one functional filler, and at least one effect pigment.

Functional fillers include, but not limited to, methyl methacrylate crosspolymer, boron nitrile, bismuth oxychloride, polymethylsilsesquioxane. They, provide optical blurring effect to minimize the appearance of fine lines, wrinkles and facial imperfections, and give rise to a more youthful appearance.

Effect pigments are typically surface treated, or untreated mineral or synthetic substances, such as titanium dioxide, mica, synthetic fluorophlogopite, or borosilicates. These effect pigments can further comprise singular or multilayer structure by coating the substance with additional titanium dioxide or iron oxides, or other coloring materials. Effect pigments in the said composition can provide a brightened and healthy radiance to its users and further enhance the overall appearance.

The aesthetic modifiers can be incorporated into the oil phase in the range of 3-12 wt % or 4-10 wt %, based on the total weight of the composition.

The oil-phase may further comprise a preservative.

A method of preparing the composition of the invention is also provided. The preparation method comprises providing an aqueous phase comprising components: water, one or more humectants, and one or more preservatives, preservative boosters and/or stabilizers; providing an oil phase comprising one or more solvents, one or more emulsifiers, one or more emollients, and one or more aesthetic modifiers; and contacting the components of the aqueous phase with the components of the oil phase to form a water-in-oil emulsion. The one or more solvents may be selected from the group consisting of diisopropyl adipate, diisopropyl sebacate, ethyl PG-acetal levulinate, ethyl glycerin acetal levulinate, triethyl citrate and a combination thereof. As a result, the composition is prepared.

A method of improving the appearance of skin in a subject is further provided. The method comprises applying the skin an effective amount of the composition of the present invention. The improving the appearance of skin may comprise treating or reducing the appearance of fine lines, wrinkles, and imperfection of skin appearance and texture.

DETAILED DESCRIPTION OF THE INVENTION

Figure 1:
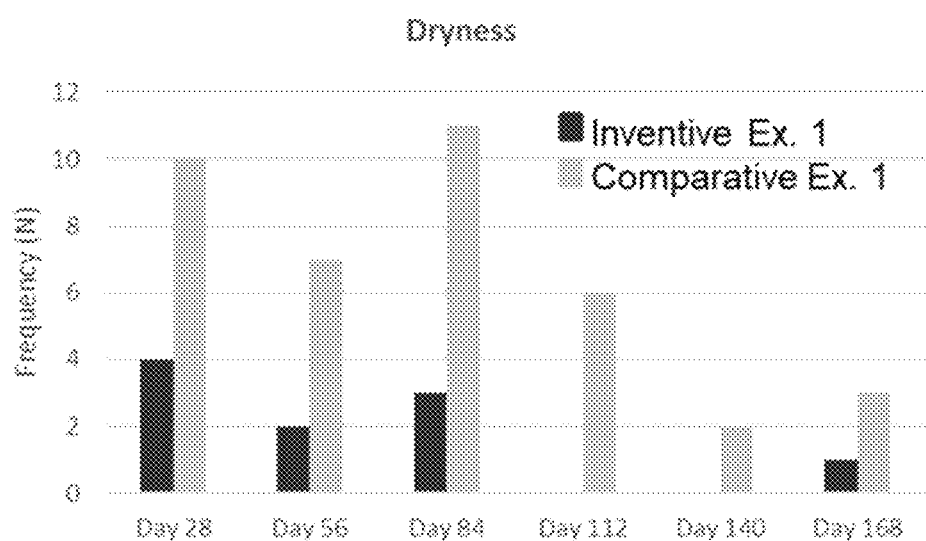
FIG. 1 shows the result of tolerability study in term of dryness.

The present invention relates to cosmetic compositions comprising one or more solvents, which may be di-acid esters and/or ethyl acetal levulinate derivatives, for solubilizing the active compound, and methods for using the compositions for treating, protecting and/or improving conditions and/or aesthetic appearance of skin. This invention was made based on the inventors' surprising discovery that stable water-in-oil emulsions comprising an oil phase with polyacid esters and/or ethyl acetal levulinate derivatives, 10% glycerin, and aesthetic modifiers could provide desirable anti-aging benefits, and an instant optical effect for reducing the appearance of fine lines and wrinkle and imperfections on skin.

Unless stated otherwise, a wt % figure for an ingredient of a composition is relative to the total weight of the composition.

The present invention provides a composition. The composition comprises an aqueous phase and an oil phase, and is a water-in-oil emulsion. The composition is stable.

The term "stable" used herein refers to a physical or chemical property of a cosmetic composition that does not change significantly over time. For example, a cosmetic composition may be deemed stable if no significant amount of change (e.g., less than about 10, 5, 1, 0.5 or 0.1 wt %) is observed in precipitation, color, pH, viscosity profile or SEM images for the cosmetic composition after storage for, for example, at least about 1, 2, 3, 4, 5, 6, 7, 8, 9, 10, 11, 12, 15, 18, 21 or 24 weeks, at a temperature of about 4-45° C., for example, at room temperature (25° C.) or 45° C., and/or atmospheric pressure (760 mmHg, i.e., 105 Pa). A composition that remains clear, without visible precipitation, for at least about 8, 12, 16, 20 or 24 hours may be deemed stable. A composition that remains clear, without visible precipitation for at least about 4- or 8-weeks at about 25° C. or 45° C. may be deemed stable.

The oil phase further comprises one or more solvents, one or more emulsifiers, one or more emollients and/or one or more aesthetic modifiers.

The solvent may be a polyacid ester or an ethyl acetal levulinate derivative. The polyacid ester may be diisopropyl adipate, acetyl tributyl citrate, triethyl citrate, dicaprylyl maleate, triisocetyl citrate, diisocetyl dodecanedioate, trioctyldodecyl citrate, diisostearyl malate, tridecyl trimellitate, tri-C14-15 alkyl citrate, di-C12-13 alkyl malate, dimyristyl tartrate, di-C12-13 alkyl tartrate, diisopropyl sebacate, tributyl citrate, diethylhexyl maleate, or di-PPG-3 myristyl ether adipate. The polyacid ester is preferably a di-acid ester such as diisopropyl adipate or diisopropyl sebacate. The ethyl acetal levulinate derivative may be ethyl PG-acetal levulinate or ethyl glycerin acetal levulinate.

The one or more solvents may be selected from the group consisting of diisopropyl adipate, diisopropyl sebacate, ethyl PG-acetal levulinate, ethyl glycerin acetal levulinate, triethyl citrate and a combination thereof. The one or more solvents selected from the group consisting of diisopropyl adipate, diisopropyl sebacate, ethyl PG-acetal levulinate, ethyl glycerin acetal levulinate, triethyl citrate and a combination thereof.

The one or more solvents may consist of two solvents. For example, the one or more solvents may be diisopropyl adipate and diisopropyl sebacate; diisopropyl adipate and ethyl PG-acetal levulinate; diisopropyl adipate and ethyl glycerin acetal levulinate; or diisopropyl adipate and triethyl citrate.

The emulsifier may be selected from the group consisting of lauryl PEG-9 polydimethylsiloxyethyl dimethicone; lauryl polyglyceryl-3 polydimethylsiloxyethyl dimethicone; dimethicone/PEG-10/15 crosspolymer; dimethicone/polyglycerin-3 crosspolymer; PEG-15/lauryl dimethicone crosspolymer; PEG-15/lauryl polydimethylsiloxyethyl dimethicone crosspolymer; lauryl dimethicone/polyglycerin-3 crosspolymer; polyglycerin-3/lauryl polydimethylsiloxyethyl dimethicone crosspolymer; cetyl PEG/PPG-10/1 dimethicone; lauryl PEG/PPG-18/18 methicone; PEG/PPG-18/18 dimethicone; and a combination thereof. The composition may comprise about 1-10 wt %, 3-9 wt % or 4-8 wt % of the emulsifier, based on the total weight of the composition.

The emollient may be selected from the group consisting of dimethicone/vinyl dimethicone crosspolymer; dimethicone/phenyl vinyl dimethicone crosspolymer; vinyl dimethicone/lauryl dimethicone crosspolymer; and a combination thereof. The composition may comprise about 5-25 wt %, 10-20 wt %, 1-014 wt % or 15-20 wt % of the emollient, based on the total weight of the composition.

The oil phase may further comprise one or more aesthetic modifiers at, for example, 3-12 wt % or 4-10 wt %, based on the total weight of the composition. The resulting composition may provide an instantly improved skin appearance.

The aesthetic modifiers include both at least one functional filler, and at least one effect pigment.

Functional fillers include, but not limited to, methyl methacrylate crosspolymer, boron nitrile, bismuth oxychloride, polymethylsilsesquioxane. They, provide optical blurring effect to minimize the appearance of fine lines, wrinkles and facial imperfections, and give rise to a more youthful appearance.

Effect pigments are typically surface treated, or untreated mineral or synthetic substances, such as titanium dioxide, mica, synthetic fluorophlogopite, or borosilicates. These effect pigments can further comprise singular or multilayer structure by coating the substance with additional titanium dioxide or iron oxides, or other coloring materials. Effect pigments in the said composition can provide a brightened and healthy radiance to its users and further enhance the overall appearance.

The oil phase may further comprise a preservative at, for example, 0.1-2 wt % or 0.12-0.18 wt %, based on the total weight of the composition. The preservative may be selected from the group consisting of p-anisic acid, phenoxyethanol, chlorphenesin, and a combination thereof.

The aqueous phase comprises water, one or more humectants, one or more preservatives, one or more preservative boosters, one or more stabilizers and/or one or more pH adjusters.

The composition may have about 20-80%, 20-70%, 20-60%, 20-50%, 20-40%, 20-30%, 30-80%, 30-70%, 30-60%, 30-50%, 30-40%, 35-65%, or 40-60% of the water.

The humectant may be glycerin, propanediol, propylene glycol, butylene glycol, dipropylene glycol or a combination thereof. The composition may comprise about 5-15 wt %, 8-12 wt % or 9-11 wt % of the humectant, based on the total weight of the composition.

The preservative in the aqueous phase may be selected from the group consisting of phenoxyethanol, chlorphenesin, p-anisic acid, and a combination thereof. The composition may comprise about 0.2-0.70 wt %, 0.25-0.40 wt % or 0.30-0.35 wt % of the preservative, based on the total weight of the composition.

The preservative booster may be disodium EDTA. The composition may comprise about 0.05-0.20 wt %, 0.75-0.15 wt % or 0.09-0.11 wt % of the preservative booster, based on the total weight of the composition.

The stabilizer may be selected from the group consisting of sodium citrate, sodium chloride, and a combination thereof. The composition may comprise about 0.1-1.5 wt %, 0.5-1.0 wt % or 0.6-0.8 wt % of the stabilizer, based on the total weight of the composition.

The pH adjuster may be citric acid. The composition may comprise about 0.01-0.05 wt % or 0.02-0.04 wt % of the pH adjuster, based on the total weight of the composition.

The composition of the present invention may be in the form of a liquid dispersion, a gel, a cream, a lotion, a mousse, or a spray. The composition may be in the form of a liquid emulsion such as a liquid-lotion, liquid-gel or liquid-cream, or a cream emulsion such as a thick cream or gel-cream, foam or mousse. The liquid emulsion form may have a thinner consistency than the cream emulsion form.

For each composition, a method of preparing the composition is provided. The preparation method comprises providing an aqueous phase, an oil phase, and contacting components of the aqueous phase with components of the oil phase to form a water-in-oil emulsion. The components of the aqueous phase comprise water, one or more humectants, one or more preservatives, one or more preservative boosters, one or more stabilizers and/or one or more pH adjusters. The components of the oil phase comprise one or more solvents, one or more emulsifiers, one or more emollients and/or one or more aesthetic modifiers.

A method of improving the appearance of skin in a subject is also provided. The method comprises applying to the skin an effective amount of the composition of the present invention. The composition is a water-in-oil emulsion comprising an aqueous phase and an oil phase. The oil phase comprises one or more solvents, one or more emulsifiers, one or more emollients, and/or one or more aesthetic modifiers. The improving the appearance of skin may comprise treating or reducing the appearance of fine lines, wrinkles, and imperfection of skin appearance and texture, for example, blemishes, dryness, roughness, dullness, age spots, sagging, and/or puffy skin.

The subject may be a consumer in need of an improved appearance of skin. The consumer may be a human. The subject may have fine lines, wrinkles, and/or imperfection of skin appearance or texture. The improved appearance of skin may be reduction of the fine lines, wrinkles, and/or imperfection of skin appearance or texture. The composition may be applied to the skin of the face, for example, around the eyes, mouth, and/or neck, of the subject.

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate.

Example 1. Emulsion Compositions

Water-in-oil (silicone) emulsion compositions were prepared by combining different solvents and then incorporating the solvent mixture into an oil phase of an emulsion. Table 1 shows the ingredients of emulsion compositions, Inventive Examples 1-4. Phase A was an oil phase, in which phase A1 comprised one or more emulsifiers, one or more solvents and solvents; phase A2 comprised one or more oil-dispersible emollients for improving sensory feel of the composition; and phase A3 comprised optionally one or more aesthetic modifiers, for example, a combination of effect pigments and/or functional fillers, for an instantly improved skin appearance. Phase B was a water phase comprising water, a humectant, one or more preservatives, preservative boosters and/or stabilizers.

In making each of Inventive Examples 1-4, the following procedure was followed. The ingredients of Phase B (aqueous phase) were mixed together in a side kettle at an ambient temperature or higher. The ingredients of Phase A (oil phase) were mixed together in a main kettle at an ambient temperature or higher. The mixture of Phase B ingredients (aqueous phase) was slowly added into the mixture of Phase A ingredients (oil phase), while mixing. As viscosity of the mixture increased, mixing speed in the main kettle was increased to about 1200 rpm. After the Phase B (aqueous phase) was mixed into Phase A (oil phase), a water-in-oil (silicone) emulsion was formed.

The stability of Inventive Examples 1-4 was evaluated in an 8-week, accelerated stability test. The emulsion compositions were stable.

TABLE 1

Emulsion Compositions

| Phase | INCI Name | Inventive Ex. 1 | Inventive Ex. 2 | Inventive Ex. 3 | Inventive Ex. 4 |
|---|---|---|---|---|---|
| A1 | LAURYL PEG-9 POLYDIMETHYLSILOXYETHYL DIMETHICONE | 1 | 1 | 1 | 2 |
| A1 | DIISOPROPYL ADIPATE | 10 | 10 | 10 | 10 |
| A1 | ETHYL PG-ACETAL LEVULINATE | | 12.5 | | |
| A1 | ETHYL GLYCERIN ACETAL LEVULINATE | | | 7 | |
| A1 | DIISOPROPYL SEBACATE | 7 | | | |
| A1 | ISOPROPYL LAUROYL SARCOSINATE | | | | 3 |
| A1 | TRIETHYL CITRATE | | | | 4 |
| A1 | p-ANISIC ACID | 0.15 | 0.15 | 0.15 | 0.15 |
| A2 | DIMETHICONE (and) DIMETHICONE/PEG-10/15 CROSSPOLYMER | 7 | 7 | 7 | 5 |
| A2 | DIMETHICONE (and) DIMETHICONE/VINYL DIMETHICONE CROSSPOLYMER | 20 | 15 | 20 | 10 |
| A3 | TITANIUM DIOXIDE (and) DIMETHICONE | 0.3 | 0.3 | 0.3 | 0.3 |
| A3 | METHYL METHACRYLATE CROSSPOLYMER | 2 | 2 | 2 | 2 |

TABLE 1-continued

| | | Emulsion Compositions | | | |
|---|---|---|---|---|---|
| Phase | INCI Name | Inventive Ex. 1 | Inventive Ex. 2 | Inventive Ex. 3 | Inventive Ex. 4 |
| A3 | BORON NITRIDE | 1 | 1 | 1 | 1 |
| A3 | BISMUTH OXYCHLORIDE | 0.4 | 0.4 | 0.4 | 0.4 |
| A3 | POLYMETHYLSILSESQUIOXANE | 2 | | | |
| A3 | MICA (and) TITANIUM DIOXIDE | 0.82 | 0.82 | 0.82 | 0.82 |
| A3 | IRON OXIDES (and) MICA | 0.08 | 0.08 | 0.08 | 0.08 |
| A3 | MICA (and) TITANIUM DIOXIDE (and) IRON OXIDES | 0.15 | 0.15 | 0.15 | 0.15 |
| B | Water (QS) | 35.99 | 37.49 | 37.99 | 48.99 |
| B | GLYCERIN | 10 | 10 | 10 | 10 |
| B | PHENOXYETHANOL | 0.5 | 0.5 | 0.5 | 0.5 |
| B | CHLORPHENESIN | 0.27 | 0.27 | 0.27 | 0.27 |
| B | HYDROXYACETOPHENONE | 0.5 | 0.5 | 0.5 | 0.5 |
| B | DISODIUM EDTA | 0.1 | 0.1 | 0.1 | 0.1 |
| B | Sodium Citrate | 0.2 | 0.2 | 0.2 | 0.2 |
| B | Sodium Chloride | 0.5 | 0.5 | 0.5 | 0.5 |
| B | CITRIC ACID | 0.04 | 0.04 | 0.04 | 0.04 |
| | Total (%): | 100 | 100 | 100 | 100 |

Example 2. Comparisons to a Benchmark Product Containing 0.15% Retinol

Comparative Ex 1, which was a benchmark product, was used in the comparative tests, it has the following ingredients list:

Water, Pentaerythrityl Tetraethylhexanoate, Dimethicone, Glycerin, PPG-15 Stearyl Ether, Cetearyl Alcohol, Stearyl Alcohol, Butylene Glycol, Ceteareth-20, Isohexadecane, Trisiloxane, Dimethicone Crosspolymer, Phenoxyethanol, Caprylyl Glycol, Ammonium Acryloyldimethyltaurate/vp Copolymer, Polyacrylamide, Polyethylene, Chlorphenesin, C13-14 Isoparaffin, Ptfe, Hydrolyzed Myrtus Communis Leaf Extract, Bht, Sodium Hyaluronate, Disodium Edta, Laureth-7, Ascorbic Acid, Polysorbate 20, Retinol, and Sodium Hydroxide.

Clinical studies were conducted using a monadic design to assess the anti-aging efficacy of test products after 6 months of use. Two test products (Inventive Ex. 1 and the benchmark product were provided to caucasian women of 40-65 years old, with mild to moderate wrinkles (grades 2 to 4 on L'Oreal Atlas 0-6 scale). The panelists were instructed to apply the test product on full face twice daily. For the bench mark product, an ease-in step was built in for tolerance adaptation, i.e. only 2 applications in Week 1 and gradually increased to twice daily starting on Week 4. A total of 121 subjects completed the study.

Self Assessment Questionnaire:

Many immediate effects were evaluated via self Assessment Questionnaire comparing Inventive Ex 1 against the benchmark product. Table 2 illustrates the outcome of the evaluation.

As shown in Table 2, at Day 0, Inventive Ex. 1 outperformed the benchmark product in improving immediate skin radiance and in improving skin healthy looking at day 0, while there was no significant difference perceived by the test subjects among other parameters.

At Day 168, there was no significant difference perceived by the test subjects among all parameters. Overall, there was no difference in subject perception of test products efficacy after 6 months' use.

TABLE 2

| | Self Assessment Questionnaire | |
|---|---|---|
| | Day 0 (Immediate post first test product application) | Comparison between test products |
| 1 | Crow's wrinkles appear less apparent | NS |
| 2 | Under eye wrinkles appear less apparent | NS |
| 3 | Under eye puffiness appears blurred/softened | NS |
| 4 | Under eye dark circles appear blurred/softened | NS |
| 5 | Skin appears radiant/glowing | Inventive Ex 1 > Comparative Ex. 1 (SS) |
| 6 | Skin looks brighter. | NS |
| 7 | The skin tone looks even. | NS |
| 8 | Dark spots appear blurred/softened | NS |
| 9 | Skin feels smooth | NS |
| 10 | Skin looks smooth. | NS |
| 11 | Skin is less oily. | NS |
| 12 | Skin feels hydrated/moisture. | NS |
| 13 | Skin looks renewed/refreshed | NS |
| 14 | Skin looks healthy | Inventive Ex 1 > Comparative Ex. 1 (SS) |
| 15 | I am happy with my skin appearance. | NS |
| | Day 168 (Evaluated with clean face) | Comparison between test products |
| 1 | Crow's feet wrinkles are not noticeable | NS |
| 2 | Under-eye wrinkles are not noticeable | NS |
| 3 | Forehead wrinkles are not noticeable | NS |
| 4 | Under eye dark circles are not noticeable | NS |
| 5 | Skin appears radiant/glowing | NS |
| 6 | Skin looks brighter. | NS |
| 7 | The skin tone looks even. | NS |
| 8 | Dark spots appear blurred/softened | NS |
| 9 | Skin feels smooth | NS |
| 10 | Skin looks smooth. | NS |
| 11 | Skin is less oily. | NS |
| 12 | Skin feels hydrated/moisture. | NS |
| 13 | Skin looks renewed/refreshed | NS |
| 14 | Skin looks healthy | NS |
| 15 | I am happy with my skin appearance. | NS |

Subjective Tolerability

Figure 2:
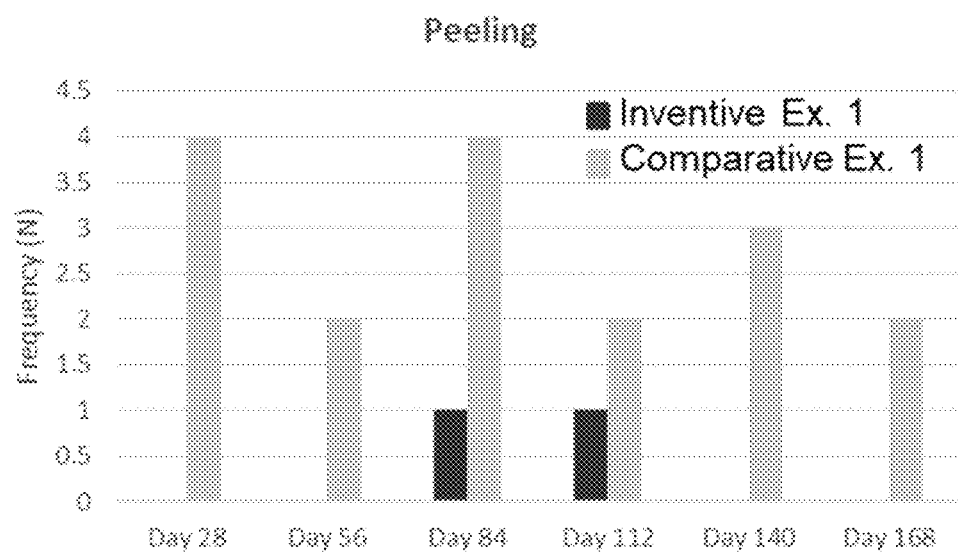
FIG. 2 shows the result of tolerability study in term of peeling.
Figure 3:
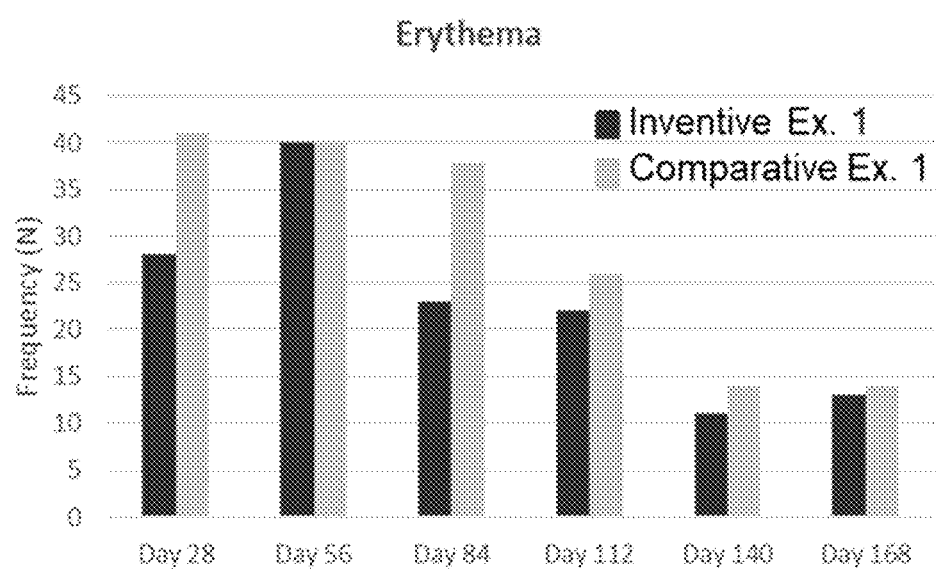
FIG. 3 shows the result of tolerability study in term of erythema.

FIGS. 1-3 show the results of tolerability study in terms of dryness, peeling and erythema, respectively. Overall, Inventive Ex. 1 was better tolerated than Comparative Ex. 1, with less drying, less peeling and less erythema.

Although the invention is illustrated and described herein with reference to specific embodiments, the invention is not intended to be limited to the details shown. Rather, various modifications may be made in the details within the scope and range of equivalents of the claims without departing from the invention.

Clinical Efficacy

Assessment was conducted by expert dermatologists by assessing (1) crow's feet wrinkle, (2) forehead wrinkle, (3) underneath eye wrinkle, (4) skin tone evenness, (5) skin tactile smoothness, (6) skin visual smoothness.

Both test products performed similarly and showed improvement over the baseline by Day 56. Both treatments improved clinical efficacy endpoints at 6 month (no difference, $p>0.1$).

No performance difference between test products at 6 month for crow's feet, forehead wrinkles and skin tone evenness.

Bioinstrumentation

Both treatments significantly improved skin hydration from baseline (SS). [SS=statistically significant]. Inventive Ex. 1 improved TEWL vs baseline at 6 month (SS). Both treatments reduced average wrinkle depth vs baseline at 6 month (SS).

Instrumental Assessment:

1. Skin hydration: Both test products significantly improved skin hydration vs. baseline from Day 28.

2. Skin barrier function (TEWL): TEWL significantly decreased vs baseline on Day 28 for Inventive Ex. 1, while Comparative Ex. 1 did not show improvement until Day 140.

3. Primos 3D image analysis of crow's feet wrinkles: wrinkle depth, wrinkle area and wrinkle count: No significant differences between treatments at each time points.

What is claimed:

1. A cosmetic composition, comprising:
   (a) an aqueous phase comprising:
      (i) water,
      (ii) one or more humectants, and
      (iii) one or more preservatives, preservative boosters and/or stabilizers; and
   (b) an oil phase comprising:
      (i) two solvents selected from the group consisting of diisopropyl adipate and diisopropyl sebacate, diisopropyl adipate and ethyl PG-acetal levulinate, diisopropyl adipate and ethyl glycerin acetal levulinate, and diisopropyl adipate and triethyl citrate,
      (ii) one or more emulsifiers, and
      (ii) one or more emollients, and
      (iv) one or more aesthetic modifiers;
   wherein the composition is a water-in-oil emulsion; and
   wherein the composition improves the appearance of skin by reducing the appearance of fine lines, wrinkles, and imperfection of skin appearance and texture.

2. The composition of claim 1, wherein the two solvents are diisopropyl adipate and diisopropyl sebacate.

3. The composition of claim 1, wherein the one or more aesthetic modifiers comprise one or more functional fillers and one or more effect pigments.

4. The composition of claim 3, wherein the functional fillers are selected from the group consisting of methyl methacrylate crosspolymer, boron nitrile, bismuth oxychloride, and polymethylsilsesquioxane.

5. The composition of claim 3, wherein the effect pigments are selected from the group consisting of surface treated mineral substances, surface treated synthetic substances, untreated mineral substances, and untreated synthetic substances.

6. The composition of claim 5, wherein the effect pigments are of a singular or multilayer structure coated with titanium dioxide, iron oxides, or a combination thereof.

7. A method of preparing a cosmetic composition, comprising the steps of:
   (a) providing an aqueous phase comprising:
      (i) water,
      (ii) one or more humectants, and
      (iii) one or more preservatives, preservative boosters and/or stabilizers;
   (b) providing an oil phase comprising:
      (v) two solvents selected from the group consisting of diisopropyl adipate and diisopropyl sebacate, diisopropyl adipate and ethyl PG-acetal levulinate, diisopropyl adipate and ethyl glycerin acetal levulinate, and diisopropyl adipate and triethyl citrate,
      (vi) one or more emulsifiers, and
      (viii) one or more emollients; and
      (viii) one or more aesthetic modifiers;
   (c) contacting the components of the aqueous phase with the components of the oil phase to form a water-in-oil emulsion.

8. A method of improving the appearance of skin in a subject, comprising applying to the skin an effective amount of the composition of claim 1.

9. The method of claim 8, wherein the improving the appearance of skin comprises reducing the appearance of fine lines, wrinkles, and imperfection of skin appearance and texture.

* * * * *